United States Patent [19]

Knaster

[11] Patent Number: 4,515,643
[45] Date of Patent: May 7, 1985

[54] METHOD FOR DETERMINING AND ADJUSTING THE POTENCY AND EFFECTIVENESS OF A METAL PHOSPHATE CONVERSION COATING PROCESS

[75] Inventor: Mark Knaster, Ambler, Pa.

[73] Assignee: Henkel Kommanditgesellschaft auf Aktien, Duesseldorf, Fed. Rep. of Germany

[21] Appl. No.: 436,481

[22] Filed: Oct. 22, 1982

[51] Int. Cl.³ .............................. C23F 7/08; C23F 7/10; C23F 7/12
[52] U.S. Cl. .......................... 148/6.15 Z; 148/6.15 R; 204/1 T; 204/404
[58] Field of Search ............... 204/1 T, 1 C, 404; 427/8; 148/6.15 Z; 324/71.1

[56] References Cited

U.S. PATENT DOCUMENTS 3,840,439  10/1974  Marsh ................................ 204/1 T
4,182,638  1/1980   Cooke ............................ 148/6.15 R

OTHER PUBLICATIONS

Nace Publication 3D170, "Modern Electrical Methods for Determining Corrosion Rates", (1970).
"Quantitative Test for Zinc Phosphate Coating Quality" by R. W. Zurilla et al., SAE Technical Paper No. 780187, Society of Automotive Engineers, Inc.
"Electrochemical Methods to Determine the Corrosion Rate of Coated Metals", by M. Piens et al., published in the Proceedings of the International Congress of Metal Corrosion, 8th, 1981, p. 1021, vol. 2, 47LJAF.

Primary Examiner—G. L. Kaplan
Attorney, Agent, or Firm—Ernest G. Szoke; Henry E. Millson, Jr.; Mark A. Greenfield

[57] ABSTRACT

An electrochemical sensor system to control the surface characteristics or coating quality of an electrically conducting surface treated with a chemical treatment solution. The sensor system operates by measuring the electrical characteristics of the electrically conducting surface. The system can be used as a quality control test and as a method for controlling the composition of the chemical treatment solution.

5 Claims, 1 Drawing Figure

METHOD FOR DETERMINING AND ADJUSTING THE POTENCY AND EFFECTIVENESS OF A METAL PHOSPHATE CONVERSION COATING PROCESS

BACKGROUND OF THE INVENTION

Methods for the electrochemical testing of a specific parameter of conversion coatings on metal surfaces are known. For example, the article "Quantitative Test for Zinc Phosphate Coating Quality" by R. W. Zurilla et al., SAE Technical Paper No. 780178, Society of Automotive Engineers, Inc., Warrendale, Pa. (paper presented during the period Feb. 27–Mar. 3, 1978 at SAE Congress and Exposition, Cobo Hall, Detroit) discloses an electrochemical test for zinc phosphate coating porosity which the authors found correlated well with salt spray performance. In a paper entitled "Electrochemical Methods to Determine the Corrosion Rate of Coated Metals", by M. Piens et al. published in the Proceedings of the International Congress of Metal Corrosion, 8th, 1981, page 1021, Volume 2, 47LJAF, the authors discuss the advantages of impedance measurements over polarization resistance in gaining insight into the behavior of the coating and the corrosion mechanism.

However, no effective electrochemical system for the determination of multiple parameters of conversion coatings has heretofore been developed, nor has a method for using these results to control the composition of the coating bath, despite the obvious need for such a system in the metal coating industry.

DESCRIPTION OF THE INVENTION

Figure 1:
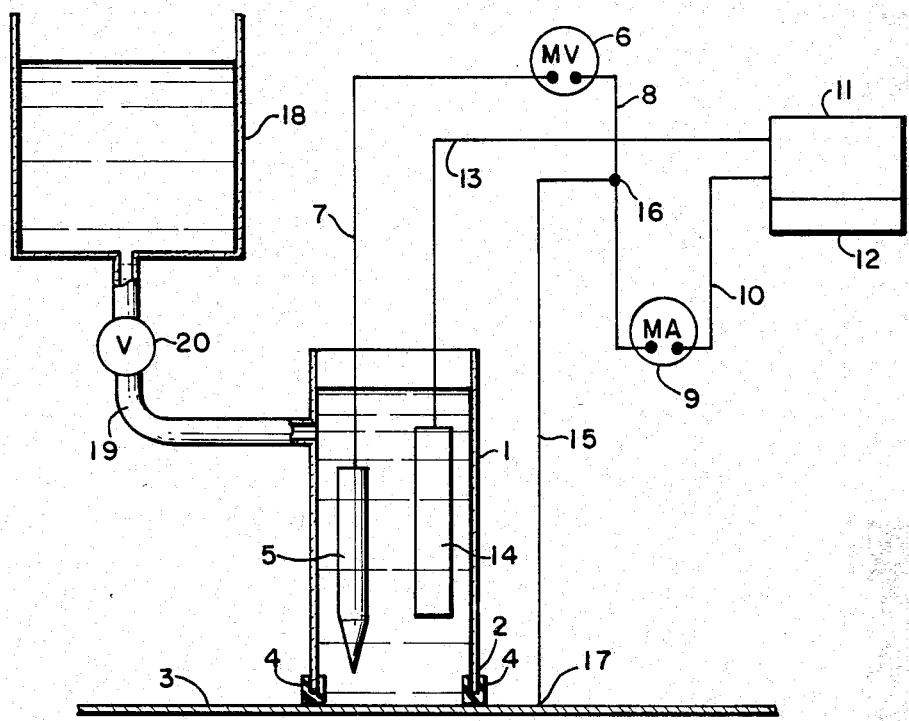
FIG. 1 is a schematic view of the sensor system of the invention.

There has now been developed a method and electrochemical sensor system for measuring the electrical characteristics of electrically conducting surfaces, which measurements can be used to control the composition of a chemical treatment solution used to treat such surfaces. In one important embodiment of the invention there has now been developed an electrochemical sensor system and method for determining a number of the characteristics of phosphate conversion coatings on metal surfaces. The system and method can also be used to determine the cleanliness of an uncoated metal surface, as well as the ability of a clean uncoated metal surface to accept an effective phosphate conversion coating. The system and method can also be used for the rapid determination of the potency of a metal phosphating bath, even to the extent of determining incipient subpotency well before noticeable degradation of the phosphate coatings has occurred.

Referring to FIG. 1, this figure shows, in schematic representation, an electrochemical cell 1, positioned with open end 2, against metal surface 3. Rubber ring 4 is attached to the rim of open end 2 to provide a liquid seal with electrically conducting surface 3. Positioned in electrochemical cell 1 is reference electrode 5. Reference electrode 5 is positioned above surface 3 and away from contact with the walls of electrochemical cell 1. Reference electrode 5 is connected to millivoltmeter 6 by electrically conducting lead 7. Millivoltmeter 6 is connected by electrically conducting lead 8 to microampmeter 9. Microampmeter 9 is attached by electrically conducting lead 10 to direct current power source 11. Power source 11 is equipped with switching means 12 adapted to provide current in either direction through the system, i.e. to provide current flow through lead 10 when switching means 12 is turned in one direction and to provide current flow through lead 13 when switching means 12 is turned in a second direction. Power source 11 is attached through electrically conducting lead 13 to counter electrode 14, which is positioned in electrochemical cell 1 above surface 3 and free of direct contact with reference electrode 5 and with the walls of electrochemical cell 1. Electrically conducting lead 15 is connected at one end 16 to lead 8, and is adapted at its other end 17 to make contact with a portion of surface 3 outside of and remote from the walls of electrochemical cell 1. Optional electrolyte reservoir 18 may be used to store electrolyte solution for use in electrochemical cell 1. Electrolyte reservoir 18 is connected through a tube or pipe 19 to electrochemical cell 1. Flow of electrolyte solution from reservoir 18 through pipe 19 into electrochemical cell 1 is controlled by stopcock or valve 20.

Electrochemical cell 1 is preferably a cylindrical cell composed of glass or another inert material which is not electrically conducting, such as plastic. Rubber ring 4 is preferably composed of an inert rubber such as neoprene, although other rubbers or plastics which will be inert to the electrolyte system, non-electrically conducting, and which will additionally provide a liquid seal when placed against surface 3 can also be used.

Reference electrode 5 can be any standard reference electrode such as a calomel electrode, a hydrogen electrode, a mercury oxide electrode, a silver oxide electrode, etc. Counter electrode 14 can be composed of any electrically conducting inert material. Examples of such materials are graphite and the noble metals such as gold, silver or platinum. Power source 11, millivoltmeter 6, and microampmeter 9 are preferably contained in a single unit. Such units containing also switching means 12 are commercially available. An example is Power Supply, Hewlett-Packard 6216-A.

Electrically conducting leads 7, 8, 10, 13 and 15 are standard commercially available wire leads. End 17 of lead 15 is adapted to make contact with the surface 3 by use of standard contact means such as electrically conducting clamps.

Using the electrochemical sensor system disclosed above the characteristics of either an uncoated metal surface or a conversion coated metal surface can be determined. Any metal surface onto which a conversion coating has been or is to be applied can be tested in the practice of the invention. For example, ferriferrous, zinciferrous, and aluminum surfaces can be tested herein whereby the process of the invention determines the characteristics of the surface.

The method of the invention for electrochemically determining the characteristics of a conversion coated or uncoated metal surface is carried out by first measuring the steady state potential of the metal surface through a dilute electrolyte solution which is placed in electrochemical cell 1 after the cell has been placed in contact with metal surface 3 as shown in FIG. 1. The electrolyte solution used in the system of FIG. 1 can be any dilute electrolyte that is nonreactive with the conversion coating and/or metal substrate with which it is to come into contact, e.g. sodium chloride, at a dilution in the range of about 0.01 to about 0.001 grams/liter.

The pH of the electrolyte solution is adjusted for proper operation of the reference electrode chosen for use in the system. For example, when a calomel electrode is employed, the pH of the solution is adjusted into the range of 10 to 12, using an aqueous inorganic alkaline solution such as a solution of sodium hydroxide. When the reference electrode is, for example, a hydrogen electrode, the pH is adjusted into the range of 3 to 4 using an acid such as hydrochloric acid. The electrolyte is added to electrochemical cell 1 until the electrolyte fully covers both reference electrode 5 and counter electrode 14. The electrolyte is conveniently added to electrochemical cell 1 by use of electrolyte reservoir 18 by opening of stopcock or valve 20 to permit the desired amount of electrolyte to flow into electrochemical cell 1.

The steady state potential of the metal surface is measured by use of reference electrode 5. By steady state potential is meant the potential of the system without the introduction of voltage or amperage from a source outside the system, i.e. power source 11 is not activated. After the steady state potential has been read on millivoltmeter 6 and recorded, a small positive or negative voltage differential compared to the steady state potential is applied by means of power source 11. By small voltage differential is meant a voltage of from about 20 millivolts to about 500 millivolts, preferably about 50 millivolts on either side of the steady state potential. The applied voltage is recorded and the resulting microamperage reading on microampmeter 9 is read and recorded. The voltage differential is then reversed and the microamperage reading obtained is read and recorded.

When employing the method of the invention on a clean metal surface, the characteristics of the surface can be determined from the readings taken above. The system can be used for determining the cleanliness of an uncoated metal surface. This is accomplished by first taking the above readings on a similar metal surface which is known to be highly clean as determined by electron microscope examination, etc. If the readings are identical or very close to those of the clean control metal surface, then it can be concluded that the metal surface being tested is also clean. In the event the readings are different from those obtained with the similar control surface, e.g. the amperage in readings from both a positive potential and a negative potential are significantly less than the readings obtained for the control, it can be concluded that the metal surface is not clean. The degree of cleanliness is also an indication of the ability of the metal surface to accept an even phosphate conversion coating.

When the method of the invention is carried out on a metal surface that contains a conversion coating, e.g. a zinc phosphate coating, the measurement of the steady state potential using a standard reference electrode is actually a measurement of the corrosion potential of the metal. The corrosion potential is believed to be a combination of three potentials from the following reactions:
  (a) oxygen reduction;
  (b) hydrogen evolution; and
  (c) metal dissolution.

The method of the invention is carried out by determining the steady state potential and the two amperage readings with a metal surface known to have an effective conversion coating thereon. For example, clean metal onto which a conversion coating has been applied using a freshly formulated zinc phosphate bath is further processed using a siccative coating such as paint and the quality of the painted surface is determined by utilizing standard tests, such as tests set forth for this purpose by the ASTM. A number of phosphate conversion coatings are applied to similar clean metal panels and readings obtained by the method of the invention are made therefrom. From these readings, a range of values is obtained for high quality conversion coatings. These ranges are then used as a standard against which similar metal surfaces coated with the coating bath are determined as the coating bath continues to be used in commercial processing of metal surfaces. So long as the metal surfaces continue to give readings within the standard ranges determined for the high quality coated metal surface, the quality of the conversion coating and the condition of the coating bath is known to be good. However, when one or more of the readings obtained are outside the standard ranges, adjustment of the coating bath may be required. The identify of the reading which has deviated from the standard, and the extent of the deviation are used to determine both the nature and the seriousness of the problem presented. For example, when the steady state potential differs from the normal range, the problem is either in the bath acidity or in the effectiveness of the final rinse. When the measurement that varies from the standard range is the cathodical current, i.e., the current coming from the counter electrode to the metal surface, then of this current is higher than the standard range, a higher level of porosity i.e. larger grain size of the conversion coating, or a lower conversion coating weight is indicated. If this current value is lower than the standard range, this indicates that a higher conversion coating weight has been applied. When the anodical current, i.e. current coming from the metal surface to the counter electrode, is higher than the standard range, this is an indication that the stability, i.e. passivity, of the metal surface is unsatisfactory. Poor stability depends in part on whether or not an adequate level of nitrite toner is present in the bath or, possibly, a problem with the quality of the final rinse.

In the event all of the measurements are outside the normal ranges, this is an indication either that the metal surface had not been adequately cleaned prior to application of the phosphate coating, or it could be an indication that a number of the bath parameters are outside their proper ranges.

The method of the invention is so sensitive that it can be used to detect the beginning of deterioration of the conversion coating while the coating is still at good commercial acceptability. Hence, the present method can be used as a quality control system on commercial production lines to control the composition of the bath on an ongoing basis so that the bath composition continually remains at its maximum potency. In addition, by having a simple method to test the quality of the conversion coating, proper use of this method will insure that no coated metal will have to be reprocessed through the coating bath or scrapped. The system can also be automated so that each coated surface, or a predetermined sampling of coated surfaces, can be tested automatically on the production line. Furthermore, the automation can also include means to signal automatic equipment controlling the composition of the chemical treatment bath, so that adjustments to the bath are made automatically.

The method of the invention also has broad applications for testing the electrical characteristics of any electrically conducting surface which has been or will be treated with a chemical treatment composition.

The method of the invention can also be used as a tool for the research and development of surface coatings. For example, the process and system of the invention can be used for rapid screening of final rinse compositions, i.e. replacements for present chemical rinses such as tri- and/or hexavalent chromium solutions, which are used to passivate the conversion coatings. Currently, the effectiveness of a final rinse composition must be determined by applying a siccative coating to a standard passivated conversion coating, and then carrying out extended corrosion tests on the painted surface to determine corrosion resistance. By using the present invention, the quality and effectiveness of final rinse solutions can be determined by measuring the anodic and cathodic current and comparing these currents, or an average of these currents, with those obtained for a known standard passivated conversion coating.

Furthermore, use of the steady state potential measurement can be used alone to determine variations in the pH of the coating baths.

The invention will be better understood from the following examples which are given for illustration purposes only and not to limit the invention.

EXAMPLE 1

The example shows that both cathodic and anodic current measured with the electrochemical sensor system of the invention increase in direct relationship to increasing grain size of a zinc phosphate conversion coating on a metal substrate.

A. Operation #1—Cleaning

A low carbon cold rolled steel (ASTM 1010) panel (4"×12") was sprayed for 60 seconds at 130° F. with a cleaning solution containing the following ingredients:

| Ingredients | grams/liter |
|---|---|
| Sodium tripolyphosphate | 2.2 |
| Sodium metasilicate | 0.8 |
| Sodium hydroxide (100%) | 4.1 |
| Surfactant (TRITON DF-16) | 1.0 |

Operation #2—The cleaned panel was given a cold water rinse for 30 seconds.

Operation #3—Substrate activation.

The panel was next sprayed for 30 seconds with a surface activating solution at 80° F. containing the following ingredients:

| Ingredients | grams/liter |
|---|---|
| Potassium titanium fluoride | 0.06 |
| Disodium phosphate | 1.14 |

Operation #4—Zinc phosphating

The panel was then sprayed in a zinc phosphating bath for 60 seconds at 130° F. with a nozzle pressure of 10 psi. The zinc phosphating bath was composed of the following ingredients:

| Ingredients | grams/liter |
|---|---|
| Phosphoric acid (100%) (H$_3$PO$_4$) | 22.9 |
| Zinc ion | 0.9 |
| Nickel ion | 0.4 |
| Sodium hydroxide (100%) | 6.9 |
| Ferric chloride, hexahydrate | 0.03 |

| Ingredients | grams/liter |
|---|---|
| Sodium chlorate (Techn.) | 0.08 |
| Sodium nitrite | 0.15 |

Operation #5—The panel was next given a cold water rinse for 30 seconds.

Operation #6—The panel was then treated with an acidulated (pH 3.7) aqueous chromate rinse solution for 10–15 seconds at ambient temperature. The acidulated aqueous rinse contained the following quantities of chromium ion:

| Ingredients | grams/liter |
|---|---|
| Cr$^{6+}$ | 0.42 |
| Cr$^{3+}$ | 0.18 |

Operation #7—The panel was treated with a deionized water rinse for 2–5 seconds at ambient temperature. The conductivity of the deionized water was less than $1.0 \times 10^{-6}$ mhos. The panel was dried by blowing with air.

The grain size of the zinc phosphate conversion coating was obtained using a Leitz Wetzlar, SM-LUX HL microscope at magnifications of 500× and 1600×. A polaroid microphotograph 3"×4" was used for measurements of crystal size by a ruler. The size of a single crystal present in the coating is represented by an average value of 10 consecutive measurements from the photomicrograph.

The grain size of this coating was <2 microns.

B. The procedure given above in A. was repeated with a second low carbon cold rolled steel (ASTM 1010) panel except that in Operation #3 the panel was sprayed with the surface activating solution for only 5 seconds.

The grain size of the resulting zinc phosphate conversion coating was between 4 and 6 microns.

C. The procedure given above in A. was repeated with a third low carbon cold rolled steel (ASTM 1010) panel except that in Operation #3 the panel was sprayed with the surface activating solution for only 1 second.

The grain size of the resulting zinc phosphate conversion coating was between 7 and 11 microns.

D. The procedure given above in A. was repeated with a fourth low carbon cold rolled steel (ASTM 1010) panel except that in Operation #3 the surface activating solution was diluted to 30% of the original concentration and the spray time was 10 seconds.

The grain size of the resulting zinc phosphate conversion coating was between 12 and 16 microns.

An electrochemical test was then performed at ambient temperature on a 1 cm$^2$ area of each of the above zinc phosphated panels using the electrochemical sensor system of the invention. The panels were contacted with the electrochemical cell 1 as shown in FIG. 1. Electrochemical cell 1 was filled with 0.01 molar NaCl solution until the reference electrode 5 and counter electrode 14 were well covered with the solution. The solution was then adjusted to pH 10 by the addition of NaOH. Reference electrode 5 was a calomel reference electrode, and counter electrode 14 was a graphite electrode. The sensor system was completed as shown in FIG. 1, using a Hewlett-Packard 6216-A Power Supply (11). The steady state potential was measured for each panel. A voltage of +50 millivolts from the steady state potential was applied by means of power source 11 and the resulting current (anodic current) measured. Then a voltage of −50 millivolts from the steady state potential was applied and the resulting current (cathodic current) measured. The results obtained for the above four phosphated panels (A. through D.) are given in Table 1 below.

TABLE 1

| Panel # | Grain Size (Microns) | Steady State Potential, Volts | Cathodic current in μA at −50 mV | Anodic current in μA at +50 mV | Average Current, μA |
|---|---|---|---|---|---|
| A. | <2 | −0.372 | 1.7 | 4 | 2.85 |
| B. | 4–6 | −0.480 | 2.4 | 5.6 | 4 |
| C. | 7–11 | −0.487 | 3 | 8.6 | 5.8 |
| D. | 12–16 | −0.484 | 4.3 | 18.8 | 11.55 |

EXAMPLE 2

The procedure of EXAMPLE 1A. was repeated with four additional low carbon cold rolled steel (ASTM 1010) panels except that the free acid level in the zinc phosphating bath in Operation #4 was changed as set forth in Table 2 below, by the addition of either phosphoric acid or sodium hydroxide.

It is known that the zinc phosphating bath used in Operation #4 gives the best conversion coatings when the free acid test is in the range of 0.6 to 0.8 mL. The free acid test measures the number of milliliters of 0.1N NaOH solution needed to titrate 10.0 milliliters of bath to a Bromphenol blue endpoint.

TABLE 2

| Panel # | Free Acid Test mL (# of mL to BPB endpoint - 10 mL bath sample) | Cathodic current in μA at −50 mV | Anodic current in μA at +50 mV | Average Current μA |
|---|---|---|---|---|
| 1 | 0.2 | 12 | 14 | 13 |
| 2 | 0.7 | 2 | 4.8 | 3.4 |
| 3 | 1.2 | 8 | 10 | 9 |
| 4 | 1.8 | 18 | 27 | 22.5 |

As can be seen from the above table the smallest average current is obtained when the free acid in the bath is at an optimum value of 0.7 mL, and the average current becomes significantly greater when the free acid is increased or decreased from the optimum value.

EXAMPLE 3

Four low carbon cold rolled steel (ASTM 1010) panels were treated in accordance with the following steps:

Operation #1—Cleaning

The panels were sprayed with the same cleaning solution as was used in Operation #1 in EXAMPLE 1A. above, by spraying the panels with the cleaning solution at 140° F. for 60 seconds.

Operation #2—The cleaned panels were rinsed in cold water for 30 seconds.

Operation #3—Iron Phosphating

The panels were sprayed with an aqueous iron phosphating bath at 160° F. for varying periods shown below, at a nozzle pressure of 10 psi.

| Panel # | Spray time, secs. |
|---|---|
| 1 | 20 |
| 2 | 35 |
| 3 | 45 |
| 4 | 60 |

The aqueous iron phosphating bath, having a pH of about 5, had the following composition:

| Ingredients | grams/liter |
|---|---|
| Phosphoric acid (100%) | 8.32 |
| Sodium carbonate | 3.3 |
| Chromium nitrate (100%) | 0.014 |
| Sodium hydroxide (100%) | 0.66 |
| Sodium chlorate | 4.63 |

Operation #4—The panels were then rinsed with cold water for 30 seconds.

Operation #5—The panels were treated with an aqueous acidulated (pH=3.7) chromate solution for 15 seconds at ambient temperature. The aqueous acidulated chromate solution contained the following quantities of chromate ions:

| Ingredient | grams/liter |
|---|---|
| $Cr^{6+}$ | 0.42 |
| $Cr^{3+}$ | 0.18 |

Operation #6—The panels were rinsed with deionized water for 2 to 5 seconds at ambient temperature, and dried by blowing with air.

The panels were then tested with the electrochemical sensor system of the invention according to the procedure described in EXAMPLE 1.

The coating weights of the panels were determined by weight difference after stripping the iron phosphate coatings from the panels using a 5% volume/volume aqueous solution of chromic acid for 5 minutes at 160° F. The panels were rinsed in cold water for 10 seconds and dried by blowing with air.

The results obtained are given in Table 3 below:

TABLE 3

| Panel # | Coating Weight mg/ft² | Cathodic current in μA at −50 μV* | Anodic current in μA at +50 mV* | Average current μA |
|---|---|---|---|---|
| 1 | 18 | 36 | 28 | 32 |
| 2 | 27 | 19 | 21 | 20 |
| 3 | 36 | 5 | 3.5 | 4.25 |
| 4 | 48 | 3.1 | 2.7 | 2.9 |

*from the steady state potential.

As can be seen from the above table, the average current is inversely proportional to the coating weight. Accordingly, when a desired coating weight is obtained for a given coating system, the electrochemical sensor of the invention can be utilized to determine undesirable variations in coating weight enabling appropriate adjustment in spray time, spray temperature, and/or bath composition.

EXAMPLE 4

This example shows the use of the sensor system and method of the invention for screening final rinse compositions for effectiveness in enhancing corrosion resistance of a conversion coating on a metal substrate.

In this example, standardized metal substrate panels are coated with a standardized conversion coating, followed by treatment with various final rinse compositions to be tested. The panels are then tested according to the sensor system and method of the invention after which the panels are coated with a standardized paint and tested for corrosion resistance using known tests and techniques.

Twelve low carbon cold rolled steel (ASTM 1010) panels (4"×12") were treated according to the procedure of EXAMPLE 1A. except that the rinse used in Operation #6 was varied from panel to panel. The aqueous rinse formulations used for each panel are given in Table 4 together with the electrochemical results obtained using the sensor system and method set forth in EXAMPLE 1.

Thereafter, the zinc phosphated panels were painted with paint system PPG 3002 by the cathodic electrodeposition coating process as the base coat, followed by painting with DuPont 922 (acrylic enamel).

As can be seen from the above table, the results of the salt spray test correlate well in a direct relationship with cathodic and anodic current, i.e. in general, the lower the cathodic and anodic current the less the paint loss in salt spray corrosion failure.

Twenty low carbon cold rolled steel (ASTM 1010) panels were treated according to the process of EXAMPLE 3, using a 60 second spray time in Operation #3, except that a different aqueous treatment solution is used in Operation #5 for each panel.

The electrochemical sensor system and method set forth in EXAMPLE 1 was used on each panel, and the results are given in Table 5.

Thereafter, the iron phosphated panels were painted with an acrylic single coat spray paint system.

The salt spray corrosion failures given in Table 5 were tested in accordance with ASTM B117 and rated in mm of corrosion creepage from the scribe. Percent-

TABLE 4

| Panel # | Operation #6 Aqueous Rinse Formulation (Zinc phosphate conversion coating on steel CRS 1010 ASTM panels) | Paint: PPG(EC) 3002 and Dupont 922 topcoat | | | SS[1] 1000 |
|---|---|---|---|---|---|
| | | Electrochemical Test (±50 mV) | | | |
| | | $E_c$ Volts | I—cathodic $\mu A$ | I—anodic $\mu A$ | hrs mm |
| 1 | Deionized water | −0.372 | 8 | 16 | 2.34 |
| 2 | 0.42 g/l $Cr^{6+}$ and 0.18 g/l $Cr^{3+}$ | −0.372 | 1.7 | 4 | Trace |
| 3 | 0.005% Phytic acid + 0.115% $H_2ZrF_6$ + $NH_4OH$ (pH = 4.45) | −0.433 | 3.5 | 15 | 1.56 |
| 4 | 0.115% $H_2ZrF_6$ (pH = 4.48) + $NH_4OH$ | −0.440 | 3.5 | 13 | 2.34 |
| 5 | 0.03% Phytic acid + 0.055% $H_2ZrF_6$ + $NH_4OH$ (pH = 4.43) | −0.436 | 25 | 27 | 12.5 |
| 6 | 0.115% $H_2ZrF_6$ + $NH_4OH$ heated to 130° F. (pH = 4.6) | −0.394 | 5.1 | 2.0 | Trace |
| 7 | 0.4% $H_2ZrF_6$ + $NH_4OH$ heated to 130° F. (pH = 4.6) | −0.424 | 14 | 23 | 2.34 |
| 8 | 0.6% $(NH_4)_2ZrF_6$ + $Na_2HPO_4$ (pH = 4.3) | −0.536 | 4.3 | 8 | 0.78 |
| 9 | 0.5% $(NH_4)_2ZrF_6$ + $Na_2HPO_4$ (pH = 5) | −0.484 | 4.1 | 2 | 0.39 |
| 10 | 0.010% Phytic acid + 0.05% $NH_4F.HF$ + $NH_4OH$ (pH = 4.3) | −0.492 | 13 | 12 | 1.56 |
| 11 | 0.01% Phytic acid + 0.115% $H_2ZrF_6$ + $NH_4OH$ (pH = 4.45) | −0.424 | 13 | 10 | 1.17 |
| 12 | 0.01% Phytic acid + 0.4% $H_2ZrF_6$ + $NH_4OH$ (pH = 4.5) | −0.333 | 3 | 6 | Trace |

[1]SS = Salt spray test ASTM B117.

ages of ingredients in the aqueous rinse formulations given in Table 5 are expressed in percent by weight.

TABLE 5

| Panel # | Operation #5 Aqueous Rinse Formulation, pH = 4.3 to 5.0 (iron phosphate conversion coating on steel CRS 1010 ASTM panels) | Paint System: Single Coat Acrylic Paint | | | | Salt Spray Test ASTM B117 250 hrs. Failure, MM average |
|---|---|---|---|---|---|---|
| | | Electrochemical Test at ± mV | | | | |
| | | SS, volts | Icathod., $\mu a$ | Ianod., $\mu a$ | Iavg., $\mu a$ | |
| 1 | Deionized water | −0.396 | 3.60 | 28.0 | 32.0 | 3.8 |
| 2 | 0.42 g/l $Cr^{6+}$ and 0.18 g/l $Cr^{3+}$ | −0.440 | 3.1 | 2.7 | 2.9 | Trace |
| 3 | 0.005% Phytic acid + 0.0092% $H_2ZrF_6$ | −0.744 | 11.0 | 10.0 | 10.5 | 0.8 |
| 4 | 0.005% Phytic acid + 0.1% $H_2ZrF_6$ | −0.722 | 4.9 | 4.4 | 4.6 | Trace |
| 5 | 0.0023% $H_2ZrF_6$ | −0.400 | 21.0 | 28.0 | 24.5 | 3.5 |
| 6 | 0.0055% $H_2ZrF_6$ | −0.660 | 13.0 | 15.0 | 14.0 | 1.0 |
| 7 | 0.052% $H_2ZrF_6$ | −0.720 | 9.0 | 8.0 | 8.5 | 0.6 |
| 8 | 0.1% $H_2ZrF_6$ | −0.664 | 6.4 | 3.0 | 4.8 | Trace |
| 9 | 0.03% Phytic acid + 0.0133% $H_2ZrF_6$ | −0.628 | 24.0 | 21.0 | 22.5 | 3.0 |
| 10 | 0.03% Phytic acid + 0.055% $H_2ZrF_6$ | −0.690 | 16.0 | 16.0 | 16.0 | 1.8 |
| 11 | 0.03% Phytic acid + 0.115% $H_2ZrF_6$ | −0.704 | 19.0 | 11.0 | 15.0 | 1.8 |
| 12 | 0.115% $H_2ZrF_6$ + 0.5% $NH_4HF_2$ | −0.704 | 19.0 | 18.0 | 18.5 | 2.5 |
| 13 | 0.5% $(NH_4)_2ZrF_6$ + $Na_2HPO_4$ | −0.740 | 10.0 | 23.0 | 16.5 | 2.8 |
| 14 | 0.6% $(NH_4)_2ZrF_6$ + $Na_2HPO_4$ | −0.646 | 8.0 | 14.0 | 11.0 | 1.0 |
| 15 | 0.1% $(NH_4)_2ZrF_6$ + $K_3PO_4$ | −0.734 | 14.0 | 15.0 | 14.5 | Trace |

TABLE 5-continued

| Panel # | Operation #5 Aqueous Rinse Formulation, pH = 4.3 to 5.0 (iron phosphate conversion coating on steel CRS 1010 ASTM panels) | Paint System: Single Coat Acrylic Paint | | | | Salt Spray Test ASTM B117 250 hrs. Failure, MM average |
|---|---|---|---|---|---|---|
| | | SS, volts | Electrochemical Test at ± mV | | | |
| | | | Icathod., μa | Ianod., μa | Iavg., μa | |
| 16 | 0.25% $H_2ZrF_6$ + $Na_2HPO_4$ | −0.580 | 9.5 | 8.8 | 9.1 | 0.8 |
| 17 | 0.1% $H_2ZrF_6$ + $Na_2HPO_4$ | −0.656 | 16.3 | 17.0 | 16.6 | 1.8 |
| 18 | 0.4% $H_2ZrF_6$ | −0.710 | 7.1 | 8.8 | 80. | Trace |
| 19 | 0.1% $H_2ZrF_6$ + $K_3PO_4$ | −0.664 | 9.1 | 8.8 | 9.0 | 0.8 |
| 20 | 0.4% $H_2ZrF_6$ at 130° F. | −0.678 | 10 | 11 | 10.5 | 1.0 |

All of the experiments set forth in Tables 4 and 5 show the correlation between the salt spray test results and the currents passing from the counter electrode to the phosphated metal surface. As can be observed from the results shown in Tables 4 and 5, when this current is larger than that for the chromic acid base rinse (Panel #2), a higher level of salt spray test failure usually resulted. Thus, by quick electrochemical measurements, the corrosion stability of conversion coatings treated with different final rinses can be determined.

EXAMPLE 5

Eight low carbon cold rolled steel (ASTM 1010) panels (4"×12") were treated in accordance with the process of EXAMPLE 3, using a spray time of 60 seconds in Operation #3, except that the pH of the iron phosphating bath in Operation #3 was varied for each panel by adding phosphoric acid or sodium hydroxide to the bath.

The panels were then tested with the electrochemical sensor system according to the procedure given in EXAMPLE 1 to determine the steady state potential of each panel. The steady state potentials obtained are given in Table 6, together with the pH of the iron phosphating bath.

TABLE 6

| Panel # | pH of Phosphating Bath (iron phosphating coating over steel CRS 1010) | Steady State Potential, Volts |
|---|---|---|
| 1 | 2.10 | −0.488 |
| 2 | 2.50 | −0.460 |
| 3 | 3.20 | −0.420 |
| 4 | 4.15 | −0.386 |
| 5 | 4.95 | −0.322 |
| 6 | 5.6 | −0.286 |
| 7 | 6.15 | −.0258 |
| 8 | 6.85 | −0.206 |

As can be seen from the above table, increasing the pH of the iron phosphating bath results in a shift of the steady state potential to the positive side. Since the optimum operating pH for this bath is known to be about 4.95, the steady state potential can be used to control the pH of the bath during commercial use, i.e. when the steady state potential varies from the value of $E_{ss} = -0.322$ (at pH 4.95), adjustment of the pH of the bath is indicated, with the direction of the potential shift showing whether the pH is too acid or too alkaline.

What is claimed is:

1. A method for determining and adjusting the potency and effectiveness of a metal phosphate conversion coating solution comprising the steps of
   (A) forming a phosphate conversion coating on a metal substrate by contacting the metal substrate with said phosphate conversion coating solution;
   (B) determining the crystallinity and thickness of the phosphate conversion coating on the metal substrate by
      a. measuring the steady state potential of the coated surface thereof through a dilute electrolyte solution in contact therewith;
      b. measuring the direct current amperage obtained when a small positive or negative voltage differential compared to the steady state potential is applied to the electrolyte solution;
      c. measuring the direct current amperage obtained when a small voltage differential compared to the steady state potential opposite to that employed in step b. is applied to the electrolyte solution; and
      d. comparing the measurement results obtained in a., b. and c. with the corresponding results obtained from use of the above identified method with a similar coated surface from a conversion coating solution of known potency;
      e. where one or more of said compared measurements are different from the measurement obtained with said similar coated surface, then adjusting the composition of the phosphate conversion coating solution as need based on the results obtained in step (B) d.

2. A method in accordance with claim 1 wherein the conversion coating solution contains both zinc ions and phosphate ions.

3. A method in accordance with claim 1 wherein the small voltage differentials applied in step (B) c. are in the range of from about 20 to about 500 millivolts above or below the steady state potential measured in step (B) a.

4. A method in accordance with claim 3 wherein said small voltage differential is about 50 millivolts in both step (B) b. and step (B) c.

5. A method in accordance with claim 1 wherein the metal substrate is ferriferrous or zinciferrous.

* * * * *